United States Patent
Holash et al.

(10) Patent No.: US 7,354,579 B2
(45) Date of Patent: *Apr. 8, 2008

(54) METHOD OF TREATING CANCER WITH A VEGF ANTAGONIST AND AN ANTI-PROLIFERATIVE AGENT

(75) Inventors: Jocelyn Holash, Amaleda, CA (US); Robert Jaffe, Tiburon, CA (US); Limin Hu, San Francisco, CA (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 394 days.

This patent is subject to a terminal disclaimer.

(21) Appl. No.: 10/897,802

(22) Filed: Jul. 23, 2004

(65) Prior Publication Data

US 2005/0032699 A1 Feb. 10, 2005

Related U.S. Application Data

(60) Provisional application No. 60/493,971, filed on Aug. 8, 2003, provisional application No. 60/490,002, filed on Jul. 25, 2003.

(51) Int. Cl.
*A61K 38/18* (2006.01)
*C07K 14/71* (2006.01)
*C12N 15/62* (2006.01)

(52) U.S. Cl. .............. 424/134.1; 424/192.1; 514/2; 514/12; 530/350; 536/23.4

(58) Field of Classification Search .......... None
See application file for complete search history.

(56) References Cited

U.S. PATENT DOCUMENTS

| 6,342,219 | B1 | 1/2002 | Thorpe | |
| 6,811,779 | B2 * | 11/2004 | Rockwell et al. | 424/135.1 |
| 6,897,294 | B2 * | 5/2005 | Davis-Smyth et al. | 530/350 |
| 2004/0265309 | A1 * | 12/2004 | Kandel et al. | 424/145.1 |

FOREIGN PATENT DOCUMENTS

WO WO00/75319 12/2000

OTHER PUBLICATIONS

Kabbinavar, F., et al., Journal of Clinical Oncology, vol. 21, No. 1 (2003), pp. 60-65.
Ferrara, N., et al. Nature Medicine, vol. 9, No. 6, (2003) pp. 669-676.
Wong, A.K., et al., PNAS, vol. 98, No. 13 (2001) pp. 7481-7486.
Kim, E.S. et al., PNAS, vol. 99, No. 17, (2002) pp. 11399-11404.
Holash, J. et al., PNAS, vol. 99, No. 17, (2002) pp. 11393-11398.
Huang, J. et al., PNAS, vol. 100, No. 13, (2003) pp. 7785-7790.

* cited by examiner

*Primary Examiner*—Christine J. Saoud
*Assistant Examiner*—Jon M Lockard
(74) *Attorney, Agent, or Firm*—Valeta Gregg, Esq.

(57) ABSTRACT

Methods of treating cancer and/or reducing or inhibiting tumor growth in a subject in need thereof, comprising administering pharmaceutical composition comprising a vascular endothelial cell growth factor (VEGF) antagonist, such as a VEGF trap, an anti-proliferative agent, such as taxol, and a pharmaceutically acceptable carrier.

17 Claims, 2 Drawing Sheets

METHOD OF TREATING CANCER WITH A VEGF ANTAGONIST AND AN ANTI-PROLIFERATIVE AGENT

CROSS-REFERENCE TO RELATED APPLICATIONS

This application claims the benefit under 35 USC § 119(e) of U.S. Provisional applications 60/490,002 filed 25 Jul. 2003 and 60/493,971 filed 8 Aug. 2003, which applications are herein specifically incorporated by reference in their entirety.

BACKGROUND

1. Field of the Invention

The field of the invention is related to methods of treating cancer in a mammal with a vascular endothelial growth factor (VEGF) antagonist in combination with an anti-proliferative agent, and pharmaceutical compositions comprising a VEGF antagonist and an anti-proliferative agent.

2. Description of Related Art

Vascular endothelial growth factor (VEGF) has been recognized as a primary stimulus of angiogenesis in pathological conditions. Approaches to methods of blocking VEGF include soluble receptor constructs, antisense molecules, RNA aptamers, and antibodies. See, for example, PCT WO/0075319, for a description of VEGF-receptor based trap antagonists.

Anti-neoplastic agents are widely used for the treatment of cancer both alone and in conjunction with surgery and/or radiation. Combination therapies using an anti-VEGF antibody and chemotherapeutic agents, such as paclitaxel (Taxol™), are known (see, for example, U.S. Pat. No. 6,342,219).

BRIEF SUMMARY OF THE INVENTION

In one aspect, the invention features a method of treating cancer in a subject in need thereof, comprising administering to the subject a vascular endothelial cell growth factor (VEGF) antagonist in combination with an anti-proliferative agent, wherein the cancer is treated. Although the subject treated may include any mammalian species, the subject in need is preferably a human suffering from cancer.

In a specific embodiment, the VEGF antagonist is a VEGF trap, capable of high affinity binding of VEGF. More specifically, the VEGF trap is Flt1D2. Flk1D3. Fc$\Delta$C1(a) or VEGFR1 R2-Fc$\Delta$C1(a) (SEQ ID NOs: 1-2). In a specific embodiment, the anti-proliferative agent is a microtubule stabilizing agent such as paclitaxel, or a derivative, analogue, such as docetaxel (Taxotere®), or mixture thereof; a platinum-based chemotherapeutic compound such as cisplatin, carboplain, iproplatin, and related compounds; or other conventional cytotoxic compounds. One commercially available form of paclitaxel is Taxol™ (Bristol-Myers Squibb).

In a second aspect, the invention features a method of decreasing, reducing, or inhibiting tumor growth in a subject in need thereof, comprising administering to the subject a vascular endothelial cell growth factor (VEGF) antagonist in combination with an anti-proliferative agent, wherein tumor growth is decreased, reduced, or inhibited.

In a third aspect, the invention features a method of reducing the amount of a chemotherapeutic agent necessary to achieve a desired therapeutic effect, comprising administering the chemotherapeutic agent with a VEGF antagonist. More specifically, the chemotherapeutic agent is an anti-proliferative agent, such as paclitaxel, or a derivative, analogue, or a mixture thereof; a platinum-based chemotherapeutic compound such as cisplatin, carboplain, iproplatin, and related compounds; or other conventional cytotoxic compounds; and the VEGF antagonist is a VEGF trap. In one embodiment, the amount of chemotherapeutic agent necessary to achieve a desired therapeutic effect, such as, for example, inhibition of tumor growth, is at least 20% less in the presence of co-administered VEGF trap. In a more specific embodiment, the amount of chemotherapeutic agent necessary is about 40-50% less in the presence of VEGF trap.

In a fourth aspect, the invention features a pharmaceutical composition comprising a vascular endothelial cell growth factor (VEGF) antagonist, an anti-proliferative agent, and a pharmaceutically acceptable carrier. In a more specific embodiment, the VEGF antagonist a VEGF trap, capable of high affinity binding of VEGF and the anti-proliferative agent is a microtubule stabilizing agent such as paclitaxel or a derivative, analogue, or mixture thereof. Even more specifically, the VEGF trap is Flt1D2. Flk1D3. Fc$\Delta$C1(a) VEGFR1R2-Fc$\Delta$C1(a) (SEQ ID NOs: 1-2), or a functionally equivalent thereof. In a preferred embodiment, the pharmaceutical composition is VEGFR1R2-Fc$\Delta$C1(a) (SEQ ID NOs: 1-2) and paclitaxel.

Other objects and advantages will become apparent from a review of the ensuing detailed description.

DETAILED DESCRIPTION

Figure 1:
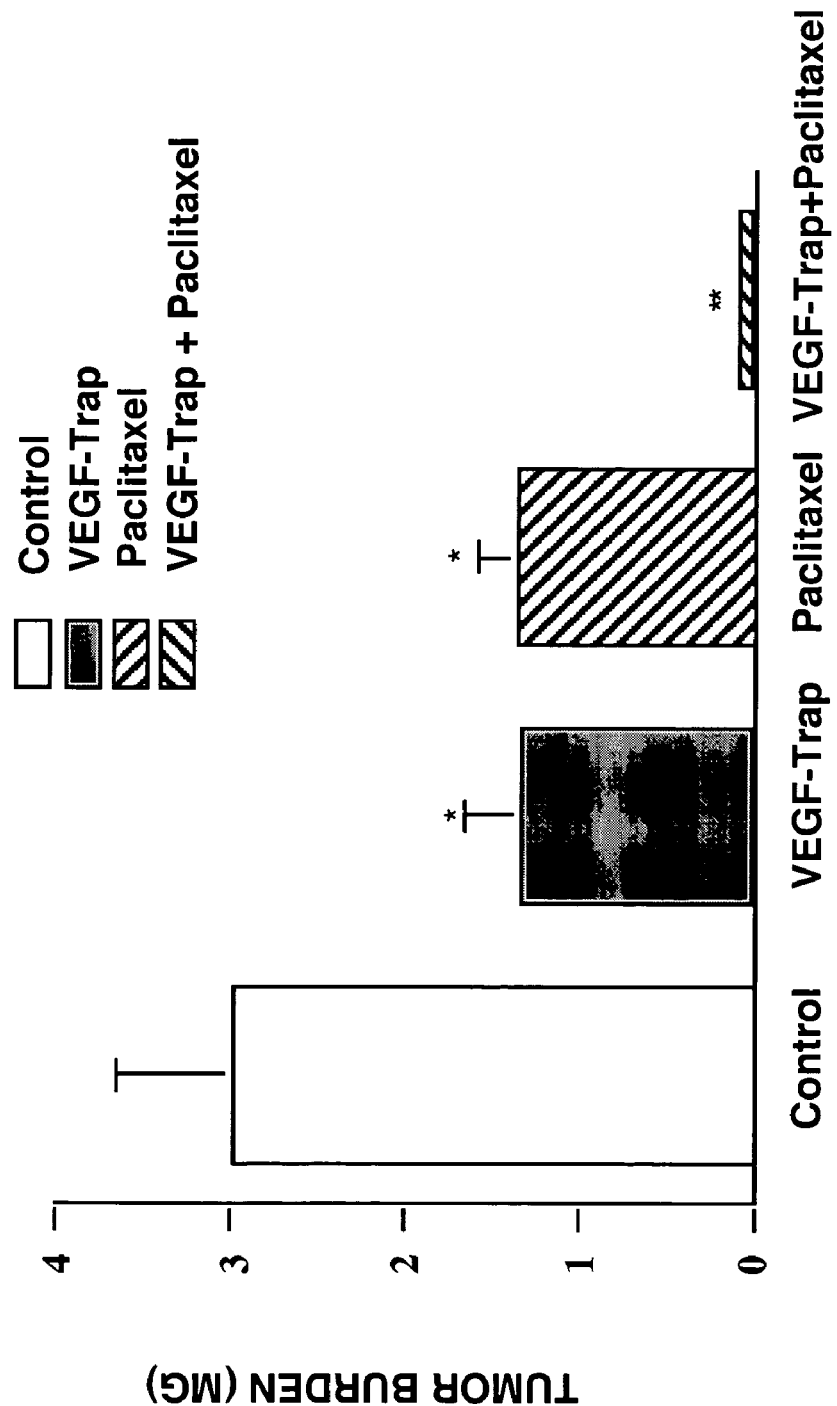
FIGS. 1-2 are bar graphs showing tumor reduction (FIG. 1) and ascites fluid volume (FIG. 2) in animals treated with vehicle alone (control), VEGF trap alone, Taxol™ alone or VEGF trap plus Taxol™.

Before the present methods and compositions are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

The invention is based on the findings that co-administration of a VEGF antagonist, for example the VEGF trap VEGFR1R2-FcΔC1(a), with an anti-proliferative agent, for example Taxol™, results in dramatic inhibition of tumor growth. The unexpected synergistic effect of the combination of a VEGF trap and paclitaxel (Taxol™) on tumor growth provides a promising therapeutic approach to the treatment of human cancer. For a description of VEGF-receptor-base antagonist VEGF traps Flt1D2.Flk1D3.FcΔC1(a) and VEGFR1R2-FcΔC1(a) (SEQ ID NOs: 1-2), see PCT WO 00/75319, the contents of which is incorporated in its entirety herein by reference.

Paclitaxel is a diterpene anticancer compound originally derived from the bark of the Taxus brevifolia (Pacific yew) tree (Wani et al. (1971) J. Am. Chem. Soc. 93:2325-2327). Taxol™ is a commercially available form of paclitaxel. Other chemotherapeutic compounds useful in combination with a VEGF antagonist in the method of the invention include, but are not limited to, docetaxel (Taxotere®; Aventis Antony, France); nitrosourea, cyclophosphamide, doxorubicin, epirubicin, 5-fluorouracil, topotecan and irinotecan, carmustine, and estramustine. Preferred chemotherapeutic agents include platinum-based compounds, such as cisplatin, carboplatin, and iproplatin. Other conventional cytotoxic chemical compounds, such as those disclosed in Wiemann et al. (1985) in *Medical Oncology* (Calabresi et al., eds.), Chapter 10, McMillan Publishing.

Methods of Administration

The invention provides methods of treatment comprising administering to a subject an effective amount of a pharmaceutical composition comprising a VEGF antagonist, such as a VEGF trap, and an anti-proliferative agent, such as paclitaxel. Various delivery systems are known and can be used to administer the composition of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as silastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and mucoadhesive.

Metronomic Chemotherapies

Metronomic chemotherapy is emerging as an improved way of administering chemotherapy. Traditional chemotherapy has been administered in single doses or short courses of therapy as the highest dose possible without causing life-threatening levels of toxicity, e.g., at the maximum tolerated dose (MTD). MTD therapy requires prolonged breaks of 2-3 weeks between successive cycles of therapy. Despite the number of such chemotherapeutics and large number of clinical trials undertaken to test them, progress has been modest in terms of curing or significantly prolonging the lives of patients with cancer (Kerbel & Kamen (2004) Nature Reviews Cancer 4:423-436).

Metronomic chemotherapy refers to the frequent, even daily, administration of chemotherapeutics at doses significantly below the MTD, with no prolonged drug-free breaks. In addition to reduced acute toxicity, the efficacy of metronomic chemotherapy seems to increase when administered in combination with specific anti-angionenic drugs, such as inhibitors of VEGF (Kerbel & Kramen (2004) supra). Accordingly, the present invention features a metronomic chemotherapy for treating cancer in a subject in need thereof, comprising administering to the subject a vascular endothelial cell growth factor (VEGF) antagonist in combination with an anti-proliferative agent, wherein the cancer is treated. In this embodiment of the invention, the VEGF antagonist and anti-proliferative agent may be administered together or sequentially for a relatively short period of time, e.g., 1-12 weeks, followed by metronomic administration of the anti-proliferative agent over a prolonged period of time, e.g., 6-24 months.

Pharmaceutical Compositions

The present invention provides pharmaceutical compositions comprising a VEGF antagonist, an anti-proliferative agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The composition of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the composition of the invention that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Kits

The invention also provides an article of manufacturing comprising packaging material and a pharmaceutical agent contained within the packaging material, wherein the pharmaceutical agent comprises at least one VEGF antagonist and at least one anti-proliferative agent, and wherein the packaging material comprises a label or package insert which indicates that the VEGF antagonist and anti-proliferative agent can be used for treating cancer or reducing tumor growth.

Specific Embodiments

As described in Example 1, mice inoculated with OVCAR3 cells were treated with either vehicle alone (control), VEGF trap alone, Taxol™ alone, or VEGF trap and Taxol™. The results showed that there was no demonstrable ascites in the mice that received VEGF trap alone or in combination with Taxol™. The combination of VEGF trap+Taxol™ resulted in a increased tumor suppression of 97%, and the mice receiving the combination treatment appeared as robust and free of side-effects as normal, non-tumor bearing animals. This experiment also demonstrates that the addition of the VEGF trap reduced the amount of the anti-proliferative agent needed to achieve an inhibition of tumor growth. Further, as described in Example 2, three of five animals receiving the combined treatment (60%) remain alive and healthy at this time, well after the end of the treatment period.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Tumor Treatment with VEGF-trap±Taxol™

Experimental Design. Two experiments, each with 4 groups of female athymic nude mice (5-7 wks, 20 mice/experiment, total n=40) were inoculated i.p. with OVCAR3 cells. Two weeks after inoculation, 1 group was treated with VEGF-Trap s.c. twice weekly+paclitaxel i.p. 3 times weekly for 4 weeks. The second group was treated with VEGF-Trap alone. The third group was treated with paclitaxel alone. The remaining group was treated with vehicle. At the end of the experiments, the mice were euthanized, the volume of ascites was measured and all visible tumor was excised and weighed.

Control of tumor growth. Tumor burden in the VEGF-Trap+paclitaxel was significantly reduced by 97.7% (p<0.01), compared to controls. Tumor burden in the VEGF-Trap alone and paclitaxel alone groups was reduced by 55.7% (p<0.05) and 54.8% (p<0.05), respectively, compared to controls (FIG. 1) (Table 1).

Figure 2:
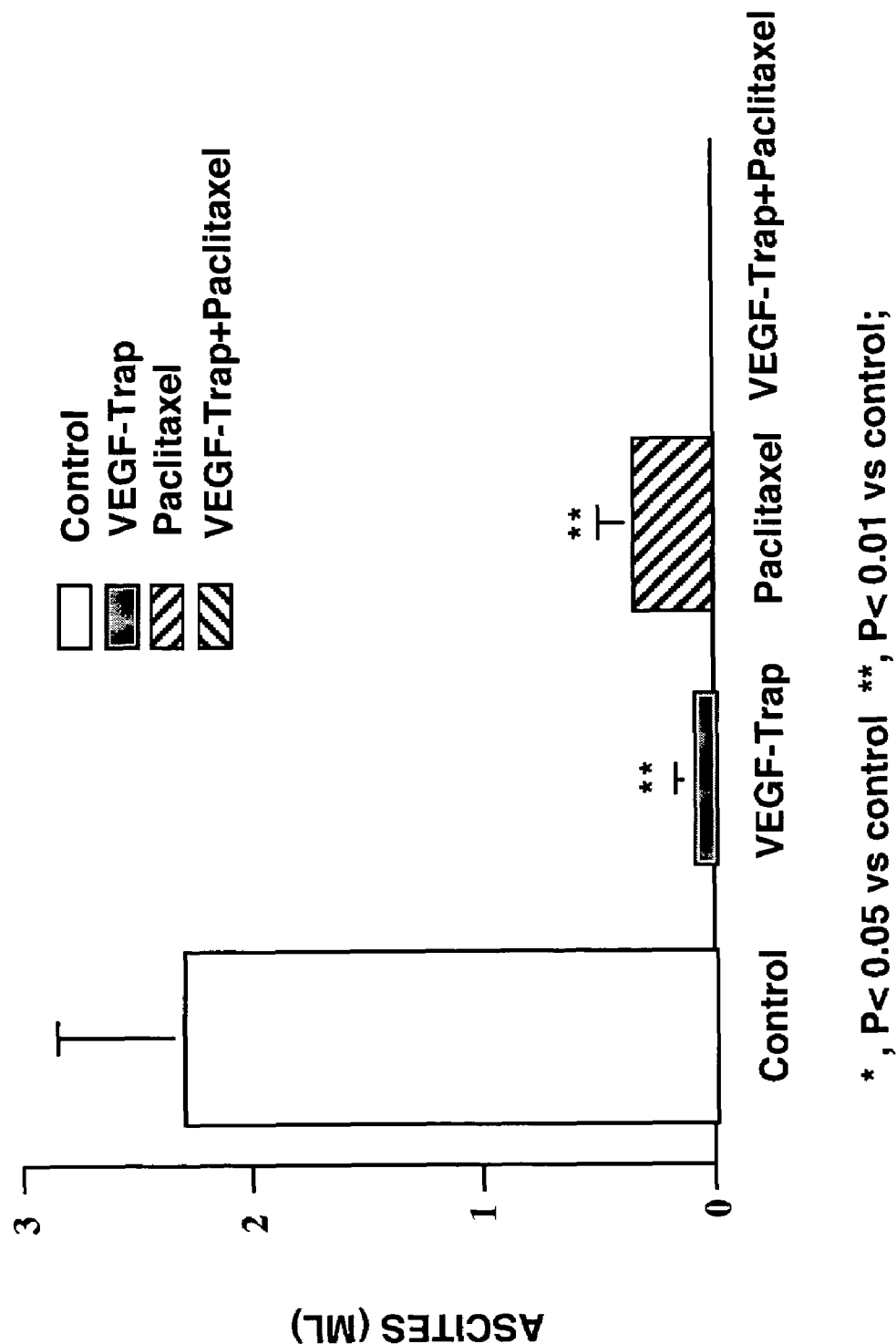

Control of ascites formation. Virtually no ascites developed in the combined treatment group or group treated with VEGF-Trap alone (FIG. 2). Paclitaxel alone significantly reduced ascites by 85.5% (p<0.01) compared to controls. Morphologic studies demonstrated that the blanched, punctate tumors were largely necrotic and avascular in the group treated with VEGF-Trap+paclitaxel. Ninety percent of mice in the untreated control and VEGF-Trap alone groups and 80% of mice in the paclitaxel alone group had tumors on the diaphragm. Ninety percent of the mice in the control group and 60% of the mice in both VEGF-Trap alone and paclitaxel alone groups had tumors in the hilus of the liver. However, tumors were not found in these locations in the combined VEGF Trap+paclitaxel groups. The appearance and behavior of the VEGF-Trap+paclitaxel group was visually indistinguishable from normal, non-inoculated mice of the same ages. These data suggest that combination therapy with VEGF-Trap plus paclitaxel may be an effective way to markedly reduce tumor burden as well as ascites formation in advanced epithelial ovarian carcinoma with minimal detectable side-effects.

TABLE 1

|  | Taxol ™ | VEGF Trap | VEGF Trap + Taxol ™ |
|---|---|---|---|
| % Reduction Ascites | 85.4 | 96.5 | 100 |
| % Reduction Tumor Burden | 55.9 | 56.7 | 97.7 |

Example 2

Effect of Treatment with VEGF-trap±Taxol™ on Survival Time

In a survival study, two groups of athymic mice were inoculated with cells from a human ovarian cancer cell line, and two weeks later were treated for four weeks with either a combination of VEGF-Trap+paclitaxel or vehicle (control) as described in Example 1 above. However, instead of sacrificing the mice at the end of four weeks, they were observed for 110 days from the time of tumor cell inoculation or until euthanasia was necessary. All of the control mice had to undergo euthanasia 5-13 days after discontinuance of treatment. In contrast, in the group of mice treated with the VEGF-Trap+paclitaxel, three of the five mice in the first group are alive, with normal eating and physical behavior 110 days after tumor cell inoculation (68 days after discontinuance of treatment). One of these has a 0.5×0.6 mm tumor at an inoculation site. A fourth mouse underwent euthanasia 89 days after tumor cell inoculation because of respiratory distress and had tumor around the trachea, and the fifth underwent euthanasia 81 days after tumor cell inoculation with bloody ascites and a 0.53 g tumor burden. A second, currently ongoing group of mice in the survival study is performing in a similar manner to the first group.

The present invention may be embodied in other specific forms without departing from the spirit or essential attributes thereof.

What is claimed:

1. A method of treating cancer in a subject in need thereof, comprising administering to the subject a VEGF antagonist and an anti-proliferative agent such that the cancer is treated, wherein the VEGF antagonist is VEGFR1R2-FcΔC1(a) comprising the amino acid sequence of SEQ ID NO:2.

2. The method of claim 1, wherein the anti-proliferative agent is a microtubule stabilizing agent.

3. The method of claim 2, wherein the anti-proliferative agent is paclitaxel, or a derivative, analogue, or mixture thereof.

4. The method of claim 1, wherein the anti-proliferative agent is a platinum-based chemotherapeutic selected from the group consisting of cisplatin, carboplatin, and iproplatin.

5. The method of claim 1, wherein the subject is a human subject.

6. A method of treating cancer in a subject in need thereof, comprising administering to the subject a vascular endothelial growth factor (VEGF) antagonist and an anti-proliferative agent such that the cancer is treated, wherein the VEGF antagonist is VEGFR1R2-FcΔC1(a) comprising the amino acid sequence of SEQ ID NO:2, and the anti-proliferative agent is a paclitaxel, docetaxel, or a derivative, analogue, or mixture thereof.

7. The method of claim 6, wherein the subject is a human subject.

8. A method of reducing tumor growth in a subject in need thereof, comprising administering to the subject a VEGF antagonist and an anti-proliferative agent, wherein the growth of the tumor is reduced, and wherein the VEGF antagonist is VEGFR1R2-FcΔC1(a) comprising the amino acid sequence of SEQ ID NO:2.

9. The method of claim 8, wherein the anti-proliferative agent is paclitaxel, docetaxel, or a derivative, analogue, or mixture thereof.

10. The method of claim 8, wherein the anti-proliferative agent is a platinum-based chemotherapeutic selected from the group consisting of cisplatin, carboplatin, and iproplatin.

11. A method of reducing ascites formation in a subject in need thereof, comprising administering to the subject a vascular endothelial cell growth factor (VEGF) antagonist in combination with an anti-proliferative agent, wherein ascites formation is inhibited, and wherein the VEGF antagonist is VEGFR1R2-FcΔC1(a) comprising the amino acid sequence of SEQ ID NO:2.

12. The method of claim 11, wherein administration is subcutaneous or intravenous.

13. A method of inhibiting or reducing tumor growth in a subject in need thereof, comprising administering to the subject a vascular endothelial cell growth factor (VEGF) antagonist in combination with an anti-proliferative agent, wherein tumor growth is inhibited, wherein the VEGF antagonist is VEGFR1R2-FcΔC1(a) comprising the amino acid sequence of SEQ ID NO:2, and the anti-proliferative agent is selected from the group consisting of paclitaxel, docetaxel or a derivative, analogue, or mixture of paclitaxel and a platinum-based chemotherapeutic.

14. A method of reducing the amount of a chemotherapeutic agent necessary to achieve a desired therapeutic effect, comprising administering the chemotherapeutic agent with a VEGF antagonist, wherein the VEGF antagonist is VEGFR1R2-FcΔC1(a) comprising the amino acid sequence of SEQ ID NO:2.

15. The method of claim 14, wherein the chemotherapeutic agent is an anti-proliferative agent selected from the group consisting of paclitaxel, or a derivative, analogue, or a mixture of paclitaxel and a platinum-based chemotherapeutic.

16. The method of claim 14, wherein the amount of a chemotherapeutic agent necessary to achieve a desired therapeutic effect is reduced by at least 20%.

17. The method of claim 16, wherein the amount of a chemotherapeutic agent necessary to achieve a desired therapeutic effect is reduced by about 30-50%.

* * * * *

SEQUENCE LISTING

```
<160> NUMBER OF SEQ ID NOS: 2

<210> SEQ ID NO 1
<211> LENGTH: 1377
<212> TYPE: DNA
<213> ORGANISM: homo sapiens

<400> SEQUENCE: 1
atggtcagct actgggacac cggggtcctg ctgtgcgcgc tgctcagctg tctgcttctc      60
acaggatcta gttccggaag tgataccggt agaccttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
gacttcaact gggaatacccc ttcttcgaag catcagcata agaaacttgt aaaccgagac     540
ctaaaaaccc agtctgggag tgagatgaag aaatttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct tccccccaaa acccaaggac     780
```

-continued

```
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aaagggcagc cccgagaacc acaggtgtac   1080
accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377
```

<210> SEQ ID NO 2
<211> LENGTH: 458
<212> TYPE: PRT
<213> ORGANISM: homo sapiens

<400> SEQUENCE: 2

```
Met Val Ser Tyr Trp Asp Thr Gly Val Leu Leu Cys Ala Leu Leu Ser
 1               5                  10                  15
Cys Leu Leu Leu Thr Gly Ser Ser Ser Gly Ser Asp Thr Gly Arg Pro
            20                  25                  30
Phe Val Glu Met Tyr Ser Glu Ile Pro Glu Ile Ile His Met Thr Glu
         35                  40                  45
Gly Arg Glu Leu Val Ile Pro Cys Arg Val Thr Ser Pro Asn Ile Thr
     50                  55                  60
Val Thr Leu Lys Lys Phe Pro Leu Asp Thr Leu Ile Pro Asp Gly Lys
 65                  70                  75                  80
Arg Ile Ile Trp Asp Ser Arg Lys Gly Phe Ile Ile Ser Asn Ala Thr
                 85                  90                  95
Tyr Lys Glu Ile Gly Leu Leu Thr Cys Glu Ala Thr Val Asn Gly His
            100                 105                 110
Leu Tyr Lys Thr Asn Tyr Leu Thr His Arg Gln Thr Asn Thr Ile Ile
        115                 120                 125
Asp Val Val Leu Ser Pro Ser His Gly Ile Glu Leu Ser Val Gly Glu
    130                 135                 140
Lys Leu Val Leu Asn Cys Thr Ala Arg Thr Glu Leu Asn Val Gly Ile
145                 150                 155                 160
Asp Phe Asn Trp Glu Tyr Pro Ser Ser Lys His Gln His Lys Lys Leu
                165                 170                 175
Val Asn Arg Asp Leu Lys Thr Gln Ser Gly Ser Glu Met Lys Lys Phe
            180                 185                 190
Leu Ser Thr Leu Thr Ile Asp Gly Val Thr Arg Ser Asp Gln Gly Leu
        195                 200                 205
Tyr Thr Cys Ala Ala Ser Ser Gly Leu Met Thr Lys Lys Asn Ser Thr
    210                 215                 220
Phe Val Arg Val His Glu Lys Asp Lys Thr His Thr Cys Pro Pro Cys
225                 230                 235                 240
Pro Ala Pro Glu Leu Leu Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
```

-continued

```
Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Gly Lys
    450                 455
```